United States Patent [19]

Hucks et al.

[11] 4,290,977

[45] Sep. 22, 1981

[54] PROCESS FOR THE PRODUCTION OF NEUTRAL PHOSPHORIC ACID ESTERS

[75] Inventors: Uwe Hucks, Alpen; Claus Wulff, Krefeld; Erhard Tresper, Krefeld; Hugo Vernaleken, Krefeld; Harald Selbeck, Krefeld, all of Fed. Rep. of Germany

[73] Assignee: Bayer Aktiengesellschaft, Leverkusen, Fed. Rep. of Germany

[21] Appl. No.: 60,736

[22] Filed: Jul. 25, 1979

[30] Foreign Application Priority Data

Jul. 29, 1978 [DE] Fed. Rep. of Germany ....... 2833342

[51] Int. Cl.$^3$ ................................................ C07F 9/09
[52] U.S. Cl. ...................................... 260/973; 260/974
[58] Field of Search ....................... 260/966, 974, 973; 546/25

[56] References Cited

U.S. PATENT DOCUMENTS

| | | | |
|---|---|---|---|
| 1,837,176 | 12/1931 | Ter Horst | 260/974 |
| 3,336,422 | 8/1967 | Peterson | 260/973 |
| 3,849,524 | 11/1974 | Colln et al. | 260/973 |

*Primary Examiner*—Anton H. Sutto
*Attorney, Agent, or Firm*—Connolly and Hutz

[57] ABSTRACT

Phosphoric acid esters are produced by the method of phase-interface condensation by reacting phosphorus oxyhalides, phosphorus pentahalides, phosphoric acid monoester dihalides or phosphoric acid diester halides with hydroxyaryl compounds in the presence of aqueous alkaline earth metal and/or alkali metal hydroxide solutions and organic water-immiscible solvents.

9 Claims, No Drawings

PROCESS FOR THE PRODUCTION OF NEUTRAL PHOSPHORIC ACID ESTERS

This invention relates to a process for the production of neutral phosphoric acid esters by reacting phosphorus oxyhalides, phosphorus pentahalides, phosphoric acid monoester dihalides or phosphoric acid diester halides with hydroxyaryl compounds in the presence of aqueous alkaline earth metal and/or alkali metal hydroxide solutions and organic water-immiscible solvents by the method of phase-interface condensation.

It is known that neutral phosphoric acid aryl esters can be produced on an industrial scale by reacting hydroxyaryl compounds, optionally in solvents and often in the presence of catalysts, with phosphorus oxychloride for example in anhydrous medium, the reaction being accompanied by the evolution of hydrogen chloride gas. One disadvantage of this process lies in the often high temperatures at which the reactions have to be carried out and which are necessary, particularly towards the end of the reaction, for removing most of the hydrogen chloride gas formed. This promotes the formation of secondary products and discolours the reaction products. To obtain pure products, the esters, some of which have high boiling points, have to be purified by such processes as vacuum distillation or recrystallisation in suitable solvents.

One particular disadvantage lies in the formation of hydrogen chloride gas. On account of the corrosion which hydrogen chloride gas causes, the constituent materials of the installations in which the esters are produced have to meet stringent requirements. In addition, it is necessary to provide special apparatus in which the hydrogen chloride gas formed is collected and absorbed, for example by water.

Accordingly, there is a need to obviate the disadvantages referred to above in the commercial production of neutral phosphoric acid aryl esters.

It has been known for some time that inter alia neutral phosphoric acid aryl esters can be produced by reacting phosphorus oxychloride with hydroxyaryl compounds at low temperatures in the presence of aqueous alkali metal hydroxide solutions using the Schotten-Baumann method [W. Autenrieth, Ber. Deutsche chem. Gesellsch. 30, 2372 (1908)].

The known disadvantages of the Schotten-Baumann reaction lie in the hydrolysis of the acid chlorides in a simultaneous secondary reaction by the aqueous alkali metal hydroxide solutions present to form the alkali metal salts of the acids on which the acid chlorides are based. The alkali metal salts of the acids thus formed no longer react with the hydroxyaryl compounds under the reaction conditions, so that the Schotten-Baumann method only gives substantially quantitative yields in special cases.

The acid chlorides of polybasic acids may undergo these secondary reactions at any stage of the main reaction. Accordingly, where dibasic or tribasic acid halides are used, good yields of neutral esters are generally not obtained.

For this reason, the "good" yields of neutral phosphoric acid aryl esters, which are not numerically quantified by Autenrieth, have to be regarded from this point of view. Repetition of Autenrieth's process gave yields which in no case exceeded 60% of the theoretical yield (Comparison Example 1).

Another disadvantage giving a smaller yield is described in U.S. Pat. No. 1,837,176. According to this patent, diphenyl phosphoric acid chloride is precipitated in solid form in the production of triphenyl phosphate by the Schotten-Baumann method and, for this reason, takes virtually no part in the further reaction. This disadvantage is overcome by adding such a small quantity of a suitable organic solvent as reaction promoter that the neutral phosphoric acid phenyl ester can still precipitate in solid form at the indicated reaction temperatures of from 0° to 3° C. The quantity of solvent used amounts to less than 10% by weight of the theoretically possible quantity of triphenyl phosphate. In addition, an attempt is made to control the hydrolysis reaction by not using an excess of alkali metal. Repetition of this process only gave yields of up to 75% of the theoretical yield (Comparison Example 2).

It has now surprisingly been found that phosphorus oxyhalides, phosphorus pentahalides, phosphoric acid monoester dihalides or phosphoric acid diester halides, when reacted with hydroxyaryl compounds in the presence of aqueous alkaline earth metal and/or alkali metal hydroxide solutions, form neutral esters in substantially quantitative yields providing an organic solvent and an excess of the hydroxyaryl compound and the alkaline earth metal and/or alkali metal hydroxide are used.

This is all the more surprising insofar as, on the basis of the foregoing, partial hydrolysis of the phosphorus oxyhalide should be accelerated by the presence of excess quantities of alkaline earth metal and/or alkali metal hydroxide.

Accordingly, the present invention relates to a process for the production of neutral phosphoric acid esters corresponding to the following general formula:

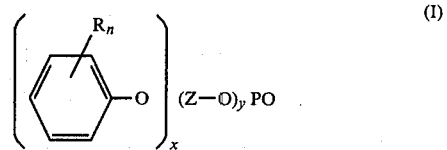

wherein

R represents a hydrogen atom, an alkyl radical containing from 1 to 20, preferably from 1 to 4 carbon atoms, an alkoxy radical containing from 1 to 20, preferably from 1 to 4 carbon atoms, a phenoxy radical, an optionally fused phenyl radical, a bicyclic fused aromatic ring system interrupted by a hetero atom, such as nitrogen, a nitrile group or a halogen atom (e.g. Cl, Br and F), n represents an integer of from 1 to 5 and the radicals R may be the same or different, x represents an integer of from 1 to 3, Z represents an alkyl radical containing from 1 to 20 carbon atoms or a radical of the following general formula:

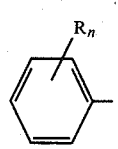

(where R and n are defined as above) and y represents the number 3−x, by reacting phosphorus oxyhalides, phosphorus pentahalides, phosphoric acid monoester dihalides or phosphoric acid diester halides corresponding to the following general formulae:

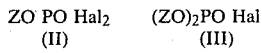

wherein Z is defined as above and Hal represents Cl and/or Br, with at least one hydroxyaryl compound corresponding to the following general formula:

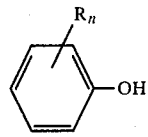

wherein R and n are defined as above, in a two-phase mixture of an organic solvent and an aqueous alkaline earth metal and/or alkali metal hydroxide solution, characterised in that both the hydroxyaryl compound and the alkaline earth metal and/or alkali metal hydroxide are used in excess, based on the phosphorus halide compound, an organic solvent being present in such quantities that from 10 to 50% by weight solutions of the neutral phosphoric acid ester are formed, and in that on completion of the reaction the organic phase is separated off and the phosphoric acid ester formed is isolated by removing the solvent.

Phosphorus oxychloride is preferably used as the phosphorus oxyhalide in the process according to the present invention. It is also possible to use phosphorus pentahalides, preferably phosphorus pentachloride. Phosphoric acid monoester dihalides or phosphoric acid diester halides, of the type which may be obtained, for example by reacting phosphorus oxyhalides with a substoichiometric quantity or organic hydroxy compounds, may also be used in the process according to the present invention. Examples of compounds such as these, which are known from the literature, are phosphoric acid monoethyl ester dichloride, phosphoric acid mono-2-ethyl hexyl ester dichloride and phosphorus diphenyl ester chloride.

Reactants for the above-mentioned phosphorus compounds which may be used in process according to the present invention are hydroxyaryl compounds corresponding to the following general formula:

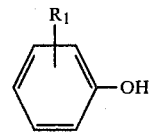

wherein

R represents a hydrogen atom, an alkyl radical containing from 1 to 20, preferably from 1 to 4 carbon atoms, an alkoxy radical containing from 1 to 20, preferably from 1 to 4 carbon atoms, a phenoxy radical, an optionally fused phenyl radical, a bicyclic aromatic ring system interrupted by a hetero atom, such as nitrogen, a nitrile group or a halogen atom (for example Cl, Br, and F) and n represents an integer of from 1 to 5 and the radicals R may be the same or different.

These compounds may be used either individually or in admixture with one another in the process according to the present invention.

Suitable compounds are, for example, phenol, o-, m- and p-cresol, o-, m- and p-isopropyl phenol, o-, m- and p-sec.-butyl phenol, o-, m- and p-tert.-butyl phenol, o-, m- and p-n-nonyl phenol, 2-ethoxy phenol, 4-phenoxy phenol, 4-phenyl phenol, o- and p-chlorophenol, o- and p-bromophenol, tribromophenol, α-naphthol or 8-hydroxy quinoline. The o-, m- and p-compounds may be used either individually or in admixture with one another.

An excess of the hydroxyaryl compound is present during the reaction. More particularly from 1.01 to 4 moles, preferably from 1.02 to 1.5 moles are preferably used per equivalent of phosphorus halide compound.

Organic, water-immiscible compounds which are inert under the reaction and conditions are generally used as solvents and/or diluents in the reaction carried out in accordance with the present invention. Examples of compounds such as these are benzene, toluene, xylene and halogenated hydrocarbons such as chlorobenzene, methylene chloride and 1,2-dichloroethane.

In one particularly advantageous embodiment of the process according to the present invention, the hydroxyaryl compounds which take part in the reaction or the esters formed during the reaction are used as solvents. To this end, the melting or setting points of these compounds must be below the reaction temperature.

The solvents are used in such quantities that preferably from 15 to 30% by weight solutions of the neutral phosphoric acid esters in the solvents used are formed.

The aqueous alkaline earth metal and/or alkali metal hydroxide solutions used may be lithium, sodium, potassium hydroxide, calcium hydroxide or ammonium hydroxide solutions. Alkali metal hydroxide solutions are preferably used. It is particularly preferred to use an aqueous sodium hydroxide solution in the process according to the present invention.

The alkaline earth metal and/or alkali metal hydroxide is used in a quantity of from 1.01 to 2 moles, preferably in a quantity of from 1.01 to 1.25 moles per equivalent of phosphorus halide compounds. The contents of pure alkaline earth metal and/or alkali metal hydroxide in the aqueous alkaline earth metal and/or alkali metal hydroxide solutions may differ within very wide limits. Concentrations of from 10 to 60% by weight are preferred, concentrations of from 25 to 53% by weight being particularly preferred. Throughout the reaction, the pH value is maintained at from 8 to 14 and is dependent upon the acidity of the hydroxyaryl compound used and of the alkaline earth metal and/or alkali metal hydroxide excess.

The use of high concentrations of alkaline earth metal and/or alkali metal hydroxide represents one particular embodiment of the process according to the present invention. After the saturation limit has been reached, the alkaline earth metal and/or alkali metal halide formed during the reaction precipitates in solid form and, on completion of the reaction, may be separated off by known methods, for example using rotary filters, stripping centrifuges or similar apparatus. Increasing the aqueous reaction phase with saturated alkaline earth metal and/or alkali metal halide solution, especially the aqueous reaction phase obtained after separation of the alkaline earth metal and/or alkali metal halide and the organic phase, can have a favourable effect on the reaction.

This variant of the present process considerably reduces the burden of alkaline earth metal and/or alkali metal halides on the effluents.

It has been found that, in general, the reaction takes place sufficiently quickly and with adequate yields in the absence of catalysts. Suitable catalysts, which in particular increase the reaction velocity, are tertiary amines, quaternary ammonium, phosphonium and sulphonium compounds such as triethylamine, n-tributylamine or tetramethyl ammonium hydroxide. The catalyst concentration may be varied within wide limits, the catalyst preferably being used in a quantity of from 0 to 0.1 mole per mole of hydroxyaryl compound used.

Particularly good yields of neutral esters are obtained by working at a temperature of from 5° to 95° C., preferably at a temperature in the range of from 25° to 50° C.

Depending on the way in which, and the temperature at which, the reaction is carried out, the reaction times range from 5 to 90 minutes and may be shortened by using catalysts.

The process according to the present invention may be carried out by mixing the hydroxyaryl compound with the alkaline earth metal and/or alkali metal hydroxide solution in a coolable stirrer-equipped vessel, optionally with the addition of water or saturated alkaline earth metal and/or alkali metal halide solution. The resulting mixture may then be combined with the phosphorus oxyhalide, phosphorus pentahalide, phosphoric acid monoester dihalide or phosphoric acid diester halide dissolved in the organic solvent with vigorous stirring at such a rate that the temperature can be controlled by cooling.

On completion of the reaction, the reaction mixture is worked up by a known method. Thus, the reaction emulsion is separated, optionally by filtration, from alkaline earth metal and/or alkali metal halides which have precipitated and the organic phase is washed with acid and then with water until free from electrolyte, for example in combined mixer/separators or separators. The solvent is distilled off. The residue left behind may be subjected to further purification, for example by distillation or crystallisation. One particular advantage, however, of the process according to the present invention lies in the fact that, where pure starting compounds are used and where the entire production of the phosphoric acid ester is carried out in an inert atmosphere, it is sufficient to evaporate the solvent because the pure light-coloured esters accumulate as residues.

The process according to the present invention may be carried out continuously in known commercial apparatus. In one particular embodiment, the solution, emulsion or suspension of the hydroxyaryl compound in aqueous alkaline earth metal and/or alkali metal hydroxide solution and the solution of the phosphorus oxyhalide, phosphorus pentahalide, phosphoric acid monoester dihalide or phosphoric acid diester halide in the solvent used are continuously introduced into and reacted in a loop reactor. The loop reactor consists of a tubular loop with a heat exchanger, a rotary pump for mixing and circulating the reaction mixture and metering units for the reactants. The reaction emulsion or suspension flows off through an outlet to a pump which delivers the reaction mixture through a flow tube in which the reaction is terminated. The flow tube is described in German Pat. No. 1,920,302 and in U.S. Pat. No. 3,674,740.

The flow tube consists of an alternating sequence of dwell sections of relatively large internal diameter and mixing sections of relatively small internal diameter, the mixing sections guaranteeing Reynold's numbers of greater than 2000.

A combination of at least three dwell sections and three mixing sections is advantageous. In one particular embodiment, the ratios of the tube diameters of the dwell sections to the mixing sections vary from 3 to 50 and their length ratio from 1 to 50.

The tube diameters of the mixing sections are so large that the flow rates in these sections correspond to Reynold's numbers of at least 2000, preferably greater than 2,300. A stable emulsion is formed during passage through the mixing tubes. The volume of the following dwell tubes and the rate of flow thus prevailing therein are gauged through the diameters selected for these tubes in such a way that no disintegration occurs and an optimal exchange of substances takes place.

In another preferred embodiment, the reaction is carried out in a cascade of stirrer-equipped vessels.

For the loop reactor/flow tube combination, the residence times amount to from 5 to 30 minutes and, for the cascade, to from 15 to 60 minutes.

The neutral phosphoric acid esters produced in accordance with the present invention may be used as plasticizers, substantially non-inflammable hydraulic oils and additives for mineral oil products.

The present invention is illustrated by the following Examples. All the percentages are used on a weight basis unless otherwise indicated.

EXAMPLE 1

169.4 g of phenol, 50 ml of toluene, 240 g of water and 155.5 g of a 45% sodium hydroxide solution are introduced into a three-necked flask equipped with a stirrer, dropping funnel and thermometer. A solution of 76.7 g of phosphorus oxychloride and 250 ml of toluene is added dropwise with vigorous stirring over a period of 20 minutes. The temperature is maintained at from 25° to 30° C. by cooling. After stirring for 30 minutes at 30° C., the phases are separated. The organic phase is washed once with 5% phosphoric acid and three times with water. The toluene is distilled off and the residue fractionated in a high vacuum. 160.2 g of pure product are obtained at 188°–190° C./0.6 Torr, corresponding to a yield of 98.2% of the theoretical yield.

EXAMPLES 2 to 7

The procedure was the same as described in Example 1. The most important parameters and the results are set out in the following Table.

| Example No. | Mole of hydroxyaryl compound per mole of phosphorus oxychloride | Mole of NaOH per mole of phosphorus oxychloride | % ester in toluene solution | Yield % of the theoretical |
|---|---|---|---|---|
| 2 | 3.6 moles m-, p-cresol (cresol 70) | 3.5 moles | 43 | 97.9 |
| 3 | 4.5 moles of m-, p-cresol | 4.0 moles | 44 | 98.9 |
| 4 | 3.6 moles of p-chlorophenol | 3.5 moles | 31 | 98.2 |
| 5 | 3.6 moles of tribromophenol | 3.5 moles | 35 | 92.1[+1] |
| 6 | 3.6 moles of α-naphthol | 3.5 moles | 33 | 93.4[+1] |
| 7 | 2.4 moles of | 2.33 moles[+3] | 32 | 96.7[+2] |

| Example No. | Mole of hydroxyaryl compound per mole of phosphorus oxychloride | Mole of NaOH per mole of phosphorus oxychloride | % ester in toluene solution | Yield % of theoretical |
|---|---|---|---|---|
| | phenol+3 | | | |

+1 isolation by crystallisation from toluene
+2 alkali wash, residue after evaporation of the toluene
+3 per mole of phosphoric acid mono-2-ethyl hexyl ester dichloride

EXAMPLE 8

1. 22.5 kg/h of a solution of
6.77 kg of phenol
5.44 kg of 50% sodium hydroxide solution and
10.29 kg of water, and
2. 18.57 kg/h of a solution of
3.07 kg of phosphorus oxychloride and
15.5 kg of toluene
are pumped into a loop reactor incorporating a heat exchanger. The reaction temperature is 27° C. and the average residence time 11.5 minutes.

After leaving the reactor, the reaction mixture is pumped through a pipe. The temperature is adjusted to 36° C. The average residence time is 8 minutes.

The phases are separated in a separating vessel. The organic solution is washed once with dilute sodium hydroxide, once with dilute phosphoric acid and twice with water in separators. After the toluene has been distilled off in a thin-layer evaporator, 6.41 kg/h of phosphoric acid triphenyl ester are obtained, corresponding to a yield of 98.2% of the theoretical yield.

COMPARISON EXAMPLE 1

141 g of phenol are dissolved in 600 g of 10% sodium hydroxide solution in a flask equipped with a stirrer and thermometer. 84.3 g of phosphorus oxychloride are introduced over a period of 13 minutes with vigorous stirring and cooling to 20° C. Towards the end of the dropwise addition, 10% sodium hydroxide solution is added to keep the pH value above 13. After stirring for 40 minutes, the organic phase is taken up in ether. The ether is distilled off and the residue recrystallised from alcohol. After drying in a drying cabinet, 96.7 g of product are weighed out. The melting point is 49° C. The yield corresponds to 59.3% of the theoretical yield.

COMPARISON EXAMPLE 2

120 g of sodium hydroxide are dissolved in 390 g of water in a flask equipped with a stirrer and thermometer. 282 g of phenol and 30 g of xylene are then introduced at room temperature. The mixture is cooled to from 0° to 3° C. 153 g of phosphorus oxychloride are then added dropwise over a period of 18 minutes. After stirring for 3 hours at 0° to 3° C., the solution is filtered. The solid fraction is taken up in xylene. After the solution has been cooled, 188 g of ester are isolated in pure form (melting point 49.3° C.) by evaporating off the xylene. After working up, another 28 g of ester are found in the mother liquor. The total yield amounts to 66.3% of the theoretical yield.

We claim:

1. In the process for the production of neutral phosphoric acid esters comprising reacting a phosphorus halide selected from the group consisting of phosphorus oxyhalides, phosphorus pentahalides, phosphoric acid monoester dihalides and phosphoric acid diester halides with at least one phenolic compound in a two phase mixture of an organic solvent and an aqueous solution of a hydroxide of an alkali metal, alkaline earth metal or mixtures thereof, the improvement comprises using 1.01 to 4 moles of said phenolic compound and 1.01 to 2 moles of said hydroxide for each mole equivalent of phosphorus halide, the organic solvent being present in sufficient amount to form a 10 to 50% by weight solution of the product neutral phosphoric acid ester and upon completion of the reaction separating the organic solvent phase from the aqueous phase and isolating the neutral phosphoric ester by removing the organic solvent.

2. A process as claimed in claim 1, characterised in that the reaction is carried out at a temperature in the range of from 5° to 95° C.

3. A process as claimed in claim 1, characterised in that the reaction is carried out at a temperature in the range of from 25° to 50° C.

4. A process as claimed in claim 1, characterised in that the reaction is carried out with an excess of hydroxyaryl compound of from 0.01 to 4 moles per equivalent of phosphorus compound.

5. A process as claimed in claim 1, characterised in that the reaction is carried out with an excess of alkaline earth metal and/or alkali metal hydroxide of from 1.01 to 2 moles per equivalent of phosphorus compound.

6. A process as claimed in claim 1, characterised in that phosphorus oxychloride or 2-ethylhexyl phosphoric acid dichloride is used as the phosphorous halide.

7. A process as claimed in claim 1, characterised in that aqueous sodium hydroxide solution having a concentration of from 10 to 60% by weight is used as the alkali metal hydroxide solution.

8. A process as claimed in claim 1, characterised in that toluene, chlorobenzene and/or methylene chloride is used as the organic solvent.

9. A process as claimed in claim 1, characterised in that the reaction is carried out continuously.

* * * * *